United States Patent [19]

Lees et al.

[11] 4,070,903
[45] Jan. 31, 1978

[54] OUTFLOW METER FOR MEASURING SURFACE DRAINAGE CHARACTERISTICS

[75] Inventors: Geoffrey Lees, Stratford-upon-Avon; Izzed-Din Katekhda, Birmingham, both of England

[73] Assignee: Dunlop Limited, London, England

[21] Appl. No.: 589,572

[22] Filed: June 23, 1975

[30] Foreign Application Priority Data

July 25, 1974 United Kingdom ............... 32956/74

[51] Int. Cl.$^2$ ............................................. G01N 15/08
[52] U.S. Cl. ............................................ 73/38; 73/146; 137/559
[58] Field of Search ..................... 73/146, 8, 55, 323, 73/37, 38; 222/510; 137/559

[56] References Cited

U.S. PATENT DOCUMENTS

| 546,554 | 9/1895 | Rabon | 222/510 X |
|---|---|---|---|
| 1,103,752 | 7/1914 | Fuegmann et al. | 222/510 X |
| 1,953,155 | 4/1934 | Currier | 73/38 X |
| 2,618,964 | 11/1952 | Byrkelt | 73/37 |
| 2,836,975 | 6/1958 | Euverard | 73/55 |
| 3,069,904 | 12/1962 | Henry | 73/146 |
| 3,203,253 | 8/1965 | Scheid | 73/146 X |
| 3,311,267 | 3/1967 | Lee et al. | 73/323 X |
| 3,548,635 | 12/1970 | Hutchinson et al. | 73/38 |
| 3,552,714 | 1/1971 | Manville | 137/559 X |
| 3,861,196 | 1/1975 | Domenighetti | 73/38 |

Primary Examiner—Daniel M. Yasich
Attorney, Agent, or Firm—Stevens, Davis, Miller & Mosher

[57] ABSTRACT

An outflow meter for measuring the drainage characteristics of a surface comprising a disc having a surface engaging face which is disposed in contact with the surface during use of the meter, an orifice extending through the disc and terminating at the surface engaging face, means for pressing the disc into engagement with the surface under a predetermined load and means for supplying a predetermined volume of fluid through the orifice to the surface engaging face characterized in that the disc is an elliptical disc.

9 Claims, 5 Drawing Figures

OUTFLOW METER FOR MEASURING SURFACE DRAINAGE CHARACTERISTICS

The present invention relates to an outflow meter for measuring the drainage characteristics of a road surface.

It is known that the skid resistance of a wet road surface decreases as the speed of a vehicle travelling over the surface increases. A comparison of the skid resistances of different road surfaces can be obtained by measuring, for each surface, the drainage characteristics of the surface, i e the ease with which a fluid can escape from beneath a tyre rolling or sliding over the surface.

The drainage characteristics of different surfaces can be compared by means of an outflow meter. This device comprises a circular rubber ring which is pressed against the road surface under a predetermined load and the time for a known volume of fluid, usually water, to flow from inside the ring through the drainage paths defined by the underside of the ring and the road surface is recorded. A comparison of the drainage characteristics of different surfaces can be obtained by pressing the rubber ring against different surfaces under the same load and comparing the time for the same volume of fluid to flow from inside the ring through the drainage paths defined by the underside of the ring and the road surface.

The rubber ring provided on outflow meters used hitherto has taken the form of a circular rubber annulus. However a circular annulus, in view of its radial symmetry, is unable to detect anisotropy in the drainage characteristics of the surfaces, should it exist, although such anisotropy might have a significant influence on the braking and cornering characteristics of a vehicle running over the surface.

The most extreme case of anisotropy in surface drainage is given by a grooved asphalt or grooved concrete surface. It has been shown that vehicles travelling in a direction parallel to such grooves experience different frictional and steering stability behaviour during braking in wet conditions from that experienced by vehicles travelling perpendicular to the grooves. This is largely, although not necessarily entirely, due to the different drainage behaviour of bulk water in the two cases.

A radially symmetrical apparatus is not able to detect such anisotropy in drainage characteristics and hence cannot correlate with variable vehicle braking performance in the two cases.

According to the present invention an outflow meter for measuring the drainage characteristics of a surface comprises an elliptical disc having a surface engaging face which is disposed in contact with the surface during use of the meter, an orifice extending through the disc and terminating at the surface engaging face, means for pressing the disc into engagement with the surface under a predetermined load and means for supplying a predetermined volume of fluid through the orifice to the surface engaging face. The drainage characteristics of a surface are assessed by measuring the time for a predetermined volume of fluid to flow from the orifice through the drainage paths defined by the surface engaging face of the disc and the surface being assessed.

The outflow meter can be positioned on a surface with the major axis of the ellipse disposed in different orientations to measure the drainage characteristics of the surface according to the direction in which a tyre moves over the surface.

The orifice may have a circular or elliptical cross-section.

A specific example of an outflow meter, according to the present invention will now be described, by way of example, with reference to the accompanying drawings in which.

Figure 1:
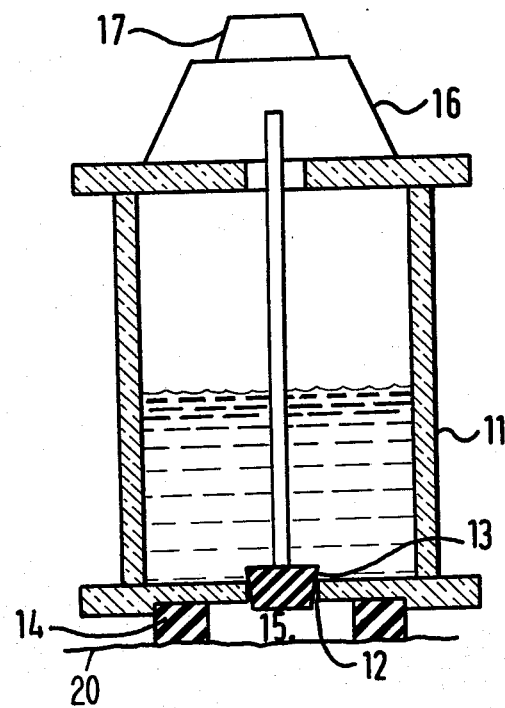
FIG. 1 is a diagrammatic representation showing a vertical section through an outflow meter.

The outflow meter illustrated in FIG. 1 comprises a transparent fluid reservoir 11 having an outlet 12 in its base closed by a rubber bung 13. An elliptical rubber disc 14 bored at its centre to provide an orifice 15 of circular cross-section is secured to the base of the reservoir so that removal of the rubber bung 13 brings the outlet 12 into fluid communication with the orifice 15.

A tripod 16 mounted on the reservoir 11 carries a weight 17.

In operation the outflow meter is located on the surface 20 whose drainage characteristics are to be tested with the exposed face of the elliptical rubber disc 14 in contact with the surface. A suitable weight 17 is placed on the tripod to press the disc 14 into engagement with the surface. The rubber bung 13 is removed and the time taken for a given volume of water to flow from the reservoir 11 through the drainage paths defined by the disc 14 and the surface is recorded as a measure of the drainage characteristics of the surface.

The outflow time is measured by the operator recording the time taken for the water level in the reservoir 11 to fall a predetermined distance. The timing can be rendered more accurate by providing two electrodes at different levels in the reservoir 11 which automatically trigger an electrical timer.

Figure 2:
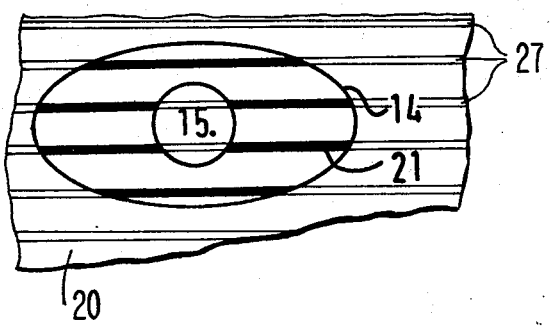
FIG. 2 shows diagrammatically an elliptical disc having a circular orifice located on a grooved surface with its major axis parallel to the grooves.
Figure 3:
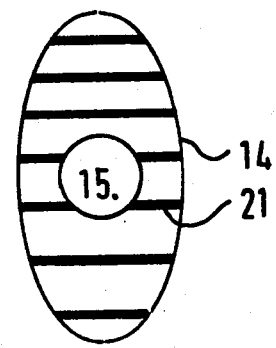
FIG. 3 shows diagrammatically an elliptical disc having a circular orifice located on a grooved surface with its major axis perpendicular to the grooves.

FIGS. 2 and 3 show an elliptical rubber disc 14 located on a surface provided with a series of parallel grooves 27 forming drainage paths 21 between the disc 14 and the surface 20. In FIG. 2 the disc 14 is positioned with its major axis parallel to the grooves 27 and in FIG. 3 with its major axis perpendicular to the grooves 27 (only paths 21 being illustrated). Since the disc 14 has a circular orifice 15 the same number of grooves 21 will be effective in drainage whether the disc 14 is located with its major axis parallel (FIG. 2) or perpendicular (FIG. 3) to the grooves 21, but the lengths of the drainage paths will differ in each case.

Figure 4:
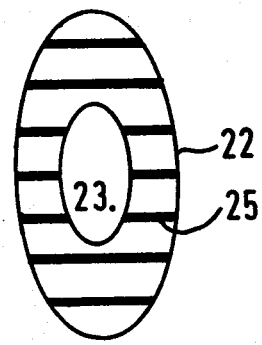
FIG. 4 shows diagrammatically an elliptical disc having an elliptical orifice located on a grooved surface with its major axis parallel to the grooves and FIG. 5 shows diagrammatically an elliptical disc having a elliptical orifice located on a grooved surface with its major axis perpendicular to the grooves.
Figure 5:
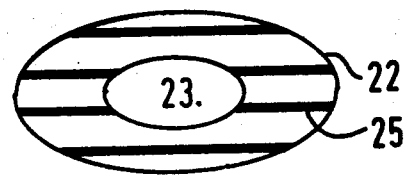

FIGS. 4 and 5 show an elliptical rubber disc 22 having an elliptical orifice 23 located on a surface (not shown) provided with parallel grooves forming drainage paths 25 between the disc 22 and the surface.

In FIG. 4 the disc 22 is positioned with its major axis parallel to the grooves and in FIG. 5 with its major axis perpendicular to the grooves. By using an elliptical disc with an elliptical orifice both the number of drainage paths and the lengths of the paths will differ according to whether the disc is located with its major axis parallel or at right angles to the grooves, i.e., there are more drainage paths and shorter drainage lengths if the disc 22 is located with its major axis at right angles to the grooves.

An artificial road surface comprising a series of parallel grooves was tested to ascertain the effect of the direction of the grooves on the outflow time from an outflow meter having an elliptical rubber disc with a circular orifice and major and minor axes measuring 90 mm and 60 mm, respectively.

The grooves in the road surfaces were located 2 mm apart. Each groove had a rectangular cross-section with a width of 1 mm and a depth of 1.2 mm.

The outflow meter was mounted on the grooved surface. Ten successive readings at half minute intervals were taken for each applied load without moving the meter. Table 1 shows the results for three different orientations of the plate on the surface, illustrating that there is a significant increase in outflow time when the major axis of the ellipse is parallel to the grooves rather than perpendicular to the grooves. The results for the case where the major axis of the ellipse is at 45° to the grooves are virtually identical to the perpendicular, i.e., transverse, illustrating that diagonal grooves would be as effective as transverse grooves in draining water from a horizontal surface under the tyre and that both are superior to longitudinal grooves.

TABLE I

Outflow times with an elliptical disc outflow meter on a grooved surface.

| Test condition | Applied load (kg) | TIME (seconds) | | | | | | | | | | |
|---|---|---|---|---|---|---|---|---|---|---|---|---|
| | | 1 | 2 | 3 | 4 | 5 | 6 | 7 | 8 | 9 | 10 | Avg |
| Major axis perpendicular to grooves | 0 | 13.0 | 13.3 | 13.8 | 13.5 | 13.3 | 13.8 | 13.7 | 13.3 | 13.3 | 13.4 | 13.4 |
| | 5 | 14.1 | 14.2 | 14.5 | 15.4 | 15.8 | 14.8 | 14.7 | 14.3 | 14.4 | 14.8 | 14.5 |
| | 10 | 15.4 | 15.8 | 15.7 | 15.7 | 15.8 | 15.4 | 15.8 | 15.3 | 15.2 | 15.3 | 15.5 |
| Major axis 45° to grooves | 0 | 12.7 | 12.7 | 13.0 | 12.8 | 12.9 | 13.1 | 13.1 | 13.3 | 13.5 | 13.3 | 13.1 |
| | 5 | 14.5 | 14.3 | 14.5 | 14.9 | 14.5 | 14.8 | 14.9 | 14.8 | 15.0 | 14.8 | 14.7 |
| | 10 | 15.8 | 15.3 | 15.5 | 15.4 | 15.2 | 15.8 | 15.4 | 15.4 | 15.5 | 15.6 | 15.5 |
| Major axis parallel to grooves | 0 | 16.2 | 15.8 | 15.9 | 15.8 | 15.6 | 15.8 | 15.9 | 15.9 | 16.0 | 16.0 | 15.9 |
| | 5 | 17.4 | 17.0 | 17.4 | 17.3 | 17.1 | 17.1 | 17.3 | 17.5 | 17.4 | 17.3 | 17.3 |
| | 10 | 18.5 | 18.4 | 18.7 | 18.7 | 18.8 | 18.5 | 18.5 | 18.4 | 18.4 | 18.6 | 18.6 |

Having now described our invention, what we claim is:

1. An outflow meter for determining the drainage characteristics of a surface, in which the time for a given volume of fluid to flow out of the meter is a measure of the drainage characteristics of the surface, said meter comprising: a liquid fluid reservoir having an outlet in its base said reservoir including means for permitting measurement of outflow time of liquid from said reservoir; a resilient disc having an elliptical surface engaging face for being selectively disposed in contact with a surface during use of the meter; an orifice extending through the disc and terminating at the surface engaging face; means for pressing the disc into engagement with a surface under a predetermined load; and closure means for the fluid reservoir outlet which closure means is removable from said outlet for bringing the outlet into fluid communication with the orifice to provide a fluid flow path from the reservoir through the orifice to the surface engaging face.

2. An outflow meter according to claim 1 wherein the orifice has a circular cross-section.

3. An outflow meter according to claim 1 wherein the orifice has an elliptical cross-section.

4. An outflow meter system for determining the drainage characteristics of a surface, in which the time for a given volume of fluid to flow out of the meter is a measure of the drainage characteristics of the surface, said meter comprising: a liquid fluid reservoir having an outlet in its base said reservoir including means for permitting measurement of outflow time of liquid from said reservoir; a resilient disc having an elliptical surface engaging face for being selectively disposed in contact with a surface during use of the meter; an orifice extending through the disc and terminating at the surface engaging face; means for pressing the disc into engagement with a surface under a predetermined load; closure means for the fluid reservoir outlet which closure means is removable from said outlet for bringing the outlet into fluid communication with the orifice to provide a fluid flow path from the reservoir through the orifice to the surface engaging face; said elliptical surface engaging face of said resilient disc being pressed into engagement with a road surface having anisotropic drainage characteristics, for measuring those anisotropic drainage characteristics.

5. The outflow meter system according to claim 4, wherein said road surface has a plurality of grooves therein.

6. The outflow meter surface according to claim 5 wherein said grooves are substantially parallel.

7. A method of determining anisotropic drainage characteristics in a road surface, comprising:
   selecting a sample road surface to be tested,
   pressing into engagement with said sample road surface an outflow meter for determining the drainage characteristics of a surface, in which the time for a given volume of liquid flow to flow out of the meter is a measure of the drainage characteristics of the surface, said meter comprising: a fluid reservoir having an outlet in its base said reservoir including means for permitting measurement of outflow time of liquid from said reservoir; a resilient disc having an elliptical surface engaging face for being selectively disposed in contact with a surface during use of the meter; an orifice extending through the disc and terminating at the surface engaging face; means for pressing the disc into engagement with a surface under a predetermined load; closure means for the fluid reservoir outlet which closure means is removable from said outlet for bringing the outlet into fluid communication with the orifice to provide a fluid flow path from the reservoir through the orifice to the surface engaging face, said elliptical surface engaging face being in engagement with said road surface;

and measuring the time required for a given volume of fluid to flow out of said meter.

8. The method of claim 7, wherein said road surface has a plurality of grooves therein.

9. The method of claim 8 wherein said grooves are substantially parallel.

* * * * *